(12) United States Patent
Mari et al.

(10) Patent No.: US 6,488,860 B2
(45) Date of Patent: *Dec. 3, 2002

(54) DEVICE AND METHOD FOR SEPARATING BLOOD INTO BLOOD COMPONENTS

(75) Inventors: Giorgio Mari, Mirandola (IT); Paolo Verri, Concordia (IT)

(73) Assignee: Fresenius AG, Bad Homburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/046,958

(22) Filed: Mar. 24, 1998

(65) Prior Publication Data
US 2002/0011452 A1 Jan. 31, 2002

(30) Foreign Application Priority Data
Mar. 24, 1997 (DE) .......................... 197 12 298

(51) Int. Cl.[7] .......................... B01D 37/00; B01D 21/26; A61M 1/00
(52) U.S. Cl. ..................... 210/806; 210/194; 210/195.1; 210/206; 210/252; 210/254; 210/257.1; 210/435; 210/749; 210/767; 210/782; 210/787; 210/805; 422/44; 494/37; 604/410
(58) Field of Search ................... 210/767, 782, 210/787, 805, 86, 97, 806, 120, 188, 749, 194, 195.1, 201, 202, 206, 218, 252, 254, 257.1, 258, 295, 435, 436, 446, 472; 604/4, 5, 406, 408, 410; 422/41, 44, 72; 494/20, 21, 37, 45

(56) References Cited
U.S. PATENT DOCUMENTS 4,596,657 A    6/1986 Wisdom ..................... 210/206
4,701,267 A *  10/1987 Watanabe et al. ........... 210/806
4,985,153 A *  1/1991 Kuroda et al. .............. 210/782
4,997,577 A *  3/1991 Stewart ....................... 210/767
5,100,564 A    3/1992 Pall et al. .................... 210/782
5,128,048 A *  7/1992 Stewart et al. .............. 210/749
5,180,504 A *  1/1993 Johnson et al. ............. 210/767
5,527,472 A *  6/1996 Bellotti et al. .............. 210/767
5,776,338 A *  7/1998 Mari .......................... 210/252

FOREIGN PATENT DOCUMENTS
EP         0 714 667        6/1996

* cited by examiner

Primary Examiner—John Kim
(74) Attorney, Agent, or Firm—Kenyon & Kenyon

(57) ABSTRACT

The invention relates to a device and a method for separating whole blood into blood components. The device has a collecting container for collecting whole blood, a primary container, and one or a plurality of satellite containers downstream from the primary container. The collecting container is connected to the primary container via a branch line containing a leucocyte filter. In addition, a bypass line is provided between the collecting container and the primary container for creating a fluid connection that circumvents the leucocyte filter. The primary container is also connected, via an additive line, to an additive container containing an additive agent for storing a blood component. The method involves collecting the donor's whole blood in the collecting container and conveying it, via the bypass line, into the primary container. The whole blood located in the primary container is then separated by centrifuigation into an erythrocyte layer and a mixed layer of blood plasma and thrombocytes. The mixed layer of blood plasma and thrombocytes is then conveyed from the primary container into the first satellite container. Subsequently, the erythrocytes in the primary container are resuspended in the additive agent, then conveyed from the primary container through the leucocyte filter into the collecting chamber.

9 Claims, 2 Drawing Sheets

DEVICE AND METHOD FOR SEPARATING BLOOD INTO BLOOD COMPONENTS

FIELD OF THE INVENTION

The invention relates to a device and a method for separating blood into blood components.

BACKGROUND OF THE INVENTION

European Patent 0 349 188 B1 discloses a device for separating blood into blood components, said device having a blood-collecting pouch which is connected via a first hose line to a primary pouch, the primary pouch being connected, via a further hose line, to a satellite pouch. In the first hose line connecting the blood-collecting pouch to the primary pouch, a filter is arranged for removing leucocytes. For extracting blood components that are free of leucocytes, a donor's whole blood is collected in the blood-collecting pouch and is conveyed to the primary pouch, via the hose line containing the filter. Subsequently, the hose line segment situated between the filter and the primary pouch is severed, the point of separation being sealed off. The primary pouch is then centrifuged, together with secondary pouch, to separate the blood contained in the primary pouch into two blood components. One of the two blood components is then conveyed, via the second hose line, into the satellite pouch. In this way, after filtration of the whole blood, leucocyte-free blood components are extracted. With the known method, a decided advantage can be seen in the fact that the pouch arrangement is centrifuged without the filter, therefore avoiding a mechanical stressing of the filter.

From U.S. Pat. No. 4,596,657, a device is known for separating blood into blood components, said device having a primary pouch which is connected, via a first hose line, to a first satellite pouch and, via a second hose line, to a second satellite pouch, containing an additive solution. In the known device, the leucocyte filter is arranged in the second hose line, which connects the primary pouch to the second satellite pouch. For extracting a leucocyte-free erythrocyte concentrate, the donor's whole blood collected in the primary pouch is first centrifuged to separate the whole blood into a mixed layer of blood plasma and thrombocytes and an erythrocyte layer. The mixed layer of blood plasma and thrombocytes is then conveyed into the first satellite pouch. Subsequently, the additive solution is conveyed from the second satellite pouch into the primary pouch. The erythrocytes resuspended in the additive solution are then conveyed from the primary pouch, via the second hose line containing the leucocyte filter, into the second satellite pouch. The known device is not designed for whole blood filtration.

U.S. Pat. No. 5,100,564 discloses a pouch system comprising a collecting pouch and two satellite pouches, each satellite pouch being connected, via hose lines, to the collecting pouch. These lines each contain a filter. The whole blood is collected in the collecting pouch and is centrifuged for separation into its components. Only then does the filtration of the individual blood components take place. The known pouch system is not designed for whole blood filtration.

U.S. Patent No. 5,527,472 discloses a pouch system comprising a collecting pouch and various further pouches connected to each other by means of flexible lines. One of the lines contains a filter. A bypass line acts to remove residual air. The known pouch system is not designed for whole blood filtration.

OBJECTS AND SUMMARY OF THE INVENTION

The invention has the objective of creating a universally usable device for separating blood into blood components, said device permitting both the filtration of only one blood component as well as the filtration of whole blood.

In addition, the invention has the objective of indicating a method which permits blood to be separated into blood components without whole blood filtration.

These and other objectives of the invention are achieved through a device having a collecting container for collecting whole blood, a primary container, one or more satellite containers downstream from the primary container and a leucocyte filter between the collecting container and the primary container. According to the invention a bypass line is provided by which blood may be routed from the collecting container to the primary container without passing through the leucocyte filter. Thus, the invention allows filtration of the whole blood provided from the collecting container or filtration of a blood component provided from the primary container.

In the device of the invention for separating blood into blood components, provision is made for a bypass line between the collecting pouch and the primary container, for creating a fluid connection, circumventing the filter. If the filtration is to be of only one blood component and not of whole blood, then the donor's blood collected in the collecting container is conveyed, via the bypass line, circumventing the filter, from the collecting container into the primary container. The blood in the primary container is then separated through centrifuging into two blood components, one of which is conveyed into a satellite container downstream from the primary container. The blood component in the primary container is then conveyed, via the line path containing the leucocyte filter, into the collecting container for separating out the leucocytes.

It is expedient if the means for opening and closing the bypass line or the collecting line are hose clamps, which are attached to the lines. The hose clamps, however, can also be added, unattached, to the hose line system.

A leucocyte-free erythrocyte concentrate is extracted by separating the whole blood in the primary container through centrifuging into an erythrocyte layer and a layer of blood plasma and thrombocytes, and the mixed layer of blood plasma and thrombocytes being conveyed into the satellite container, the erythrocytes remaining in the primary container. To extract leucocyte-free erythrocyte concentrate, the erythrocytes are then conveyed, via the line path containing the leucocyte filter, into the collecting container. The collecting container can then be disconnected and the point of separation sealed off.

Alternatively, with the device of the invention, it is also possible to separate the blood components in accordance with the method described in European Patent 0 349 188 B1. For this purpose, the bypass line is interrupted and the whole blood is first conveyed to the primary container, via the line path containing the leucocyte filter, before it is separated by centrifuging into the individual blood components. In this context, the leucocyte filter is designed such that it can be operated in two directions, i.e., the filter connections can be used both as inlet and outlet.

For extracting a leucocyte-free erythrocyte concentrate from whole blood, a separating device having only one satellite container is sufficient. An advantageous specific embodiment of the separating device comprises a second satellite container, downstream from the first satellite container, so that, in a second centrifuging step, the blood components in the first satellite container can be separated out and the separated-out blood components conveyed into the second satellite container.

In a preferred specific embodiment of the separating device, provision is made for an additive container, which is connected to a primary container via an additive line. The additive container is filled with a solution used for storing a blood component. This solution can be added to the blood component remaining in the primary container.

In a preferred refinement, the first collecting line, which connects the collecting container to the filter inlet, and/or the second collecting line, which connects the filter outlet to the primary container, is designed as a line which can be divided or sealed off or clamped off, e.g., a PVC line, so that the collecting container can be easily separated for storing the leucocyte-free blood components, or the leucocyte filter can be separated from the primary container before the centrifuging, as the case may be. For interrupting the fluid connection, conventional hose clamps can be provided on the hose lines. However, even in the known methods, the hose lines can be heat-sealed after separation.

In the following, two exemplary embodiments of the invention are explained in detail with reference to the drawings.

DETAILED DESCRIPTION OF THE PREFERRED EMBODIMENTS

Figure 1:
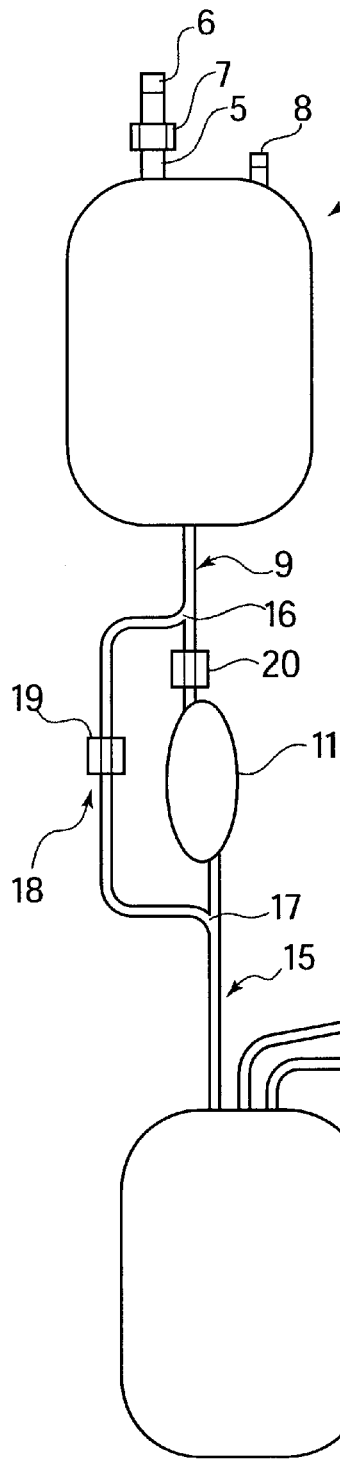
FIG. 1 shows a first specific embodiment of a device for separating blood into blood components, said device having a satellite container, in schematic representation.
Figure 1:
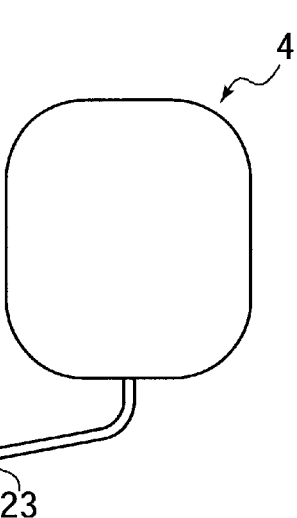

One specific embodiment of a device for separating blood into blood components comprises a collecting container 1, a primary container 2, a satellite container 3, and an additive container 4, which are constituted as film-sheet pouches (FIG. 1). Collecting pouch 1 containing an anti-coagulation agent has a connecting line 5 having a Luer-lock connector 6 for connecting to an undepicted blood supply line, which is provided with a cannula. However, the blood supply line having the cannula can also be a component part of the separating device. For clamping off connecting line 5, a hose clamp 7 is provided on it. In addition, collecting pouch 1 is provided with a spike-connector 8 for connecting an undepicted hose line for subsequent conveyance to the patient of the blood component collected in the collecting pouch.

Figure 2:
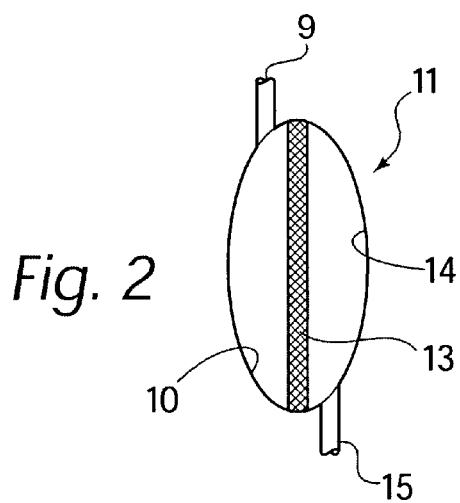
FIG. 2 shows a section of the filter for removing leucocytes.

Collecting pouch 1 is connected, via a first collecting line 9, to first chamber 10 of a filter 11 for removing leucocytes, said filter 11 being subdivided by a filter material 13 into first chamber 10 and a second chamber 14 (FIG. 2). Second chamber 14 of leucocyte filter 11 is connected, via a second collecting line 15, to primary pouch 2. First and second collecting lines 9, 15 are PVC lines which can be separated and sealed, liquid-tight, with the known heat-sealing devices.

Between collecting pouch 1 and leucocyte filter 11, first collecting line 9 has a first branch-off 16, while second collecting line 15 has a second branch-off 17 between filter 11 and primary pouch 2. For circumventing the line path 9, 15 running through leucocyte filter 11, provision is made for a bypass line 18 whose ends are connected to first and second branches-off 16 and 17, respectively.

On bypass line 18 and on the segment of first collecting line 9, situated between first branch-off 16 and leucocyte filter 11, provision is made for line clamps 19 and 20, respectively. In place of hose clamps 19, 20 on bypass line 18 or first collecting line 9, respectively, provision can also be made for two-way valves in first and second collecting line 9, 15, respectively.

Primary pouch 2 is connected to first satellite pouch 3 via a first transfer line 21 which is provided with a hose clamp 22. Additive pouch 4, filled with an additive solution for storing erythrocytes, is connected to primary pouch 2, via an additive line 23, which is provided with a hose clamp 24. The additive solution is, e.g., a solution (SAGM solution) containing sodium chloride (140 mmol/l), adenine (1.25 mmol/l), glucose (46 mmol/l) and mannitol (29 mmol/l).

The method for extracting leucocyte-free erythrocyte concentrate from whole blood is described in detail below.

After all the hose clamps are closed, a blood supply line having a cannula for reception of donor blood is connected to Luer-lock connector 6 of connecting line 5, and hose clamp 7 of the connecting line is opened. After filling collecting pouch 1 with the donor's blood, hose clamp 7 is closed once again. Then hose clamp 19 of bypass line 18 is opened, so that the blood from collecting pouch 1 flows by gravity into primary pouch 2. Then hose clamp 19 of the bypass line is closed once again, and the blood in primary pouch 2 is separated in a known manner by centrifuging into an erythrocyte layer and a mixed layer of blood plasma and thrombocytes (PRP). Then, after opening hose clamp 22 of transfer line 21, mixed layer, lying on top, of blood plasma and thrombocytes is conveyed into satellite pouch 3. Then hose clamp 22 of transfer line 21 is closed once again, and hose clamp 24 of additive line 23 is opened once again, to convey the additive solution by gravity into primary pouch 2. Then, after the opening of hose clamp 20 of first collecting line 9, the erythrocytes resuspended in the solution are once again conveyed, via the line path containing leucocyte filter 11, into collecting pouch 1, whereupon hose clamp 20 is closed once again. Then first collecting line 9 is divided above first branch-off 16, and the point of separation is sealed off so that collecting pouch 1 containing the leucocyte-free erythrocyte concentrate can be removed.

If hose clamp 19 of bypass line 18 is closed and the hose clamp of first collecting line 9 is opened, then, optionally, the whole blood initially collected in collecting pouch 1 is filtered, in accordance with the method described above for removing leucocytes, in order then to separate out the individual blood components. In this regard, reference is expressly made once again to European Patent 0 349 188 B1.

Figure 3:
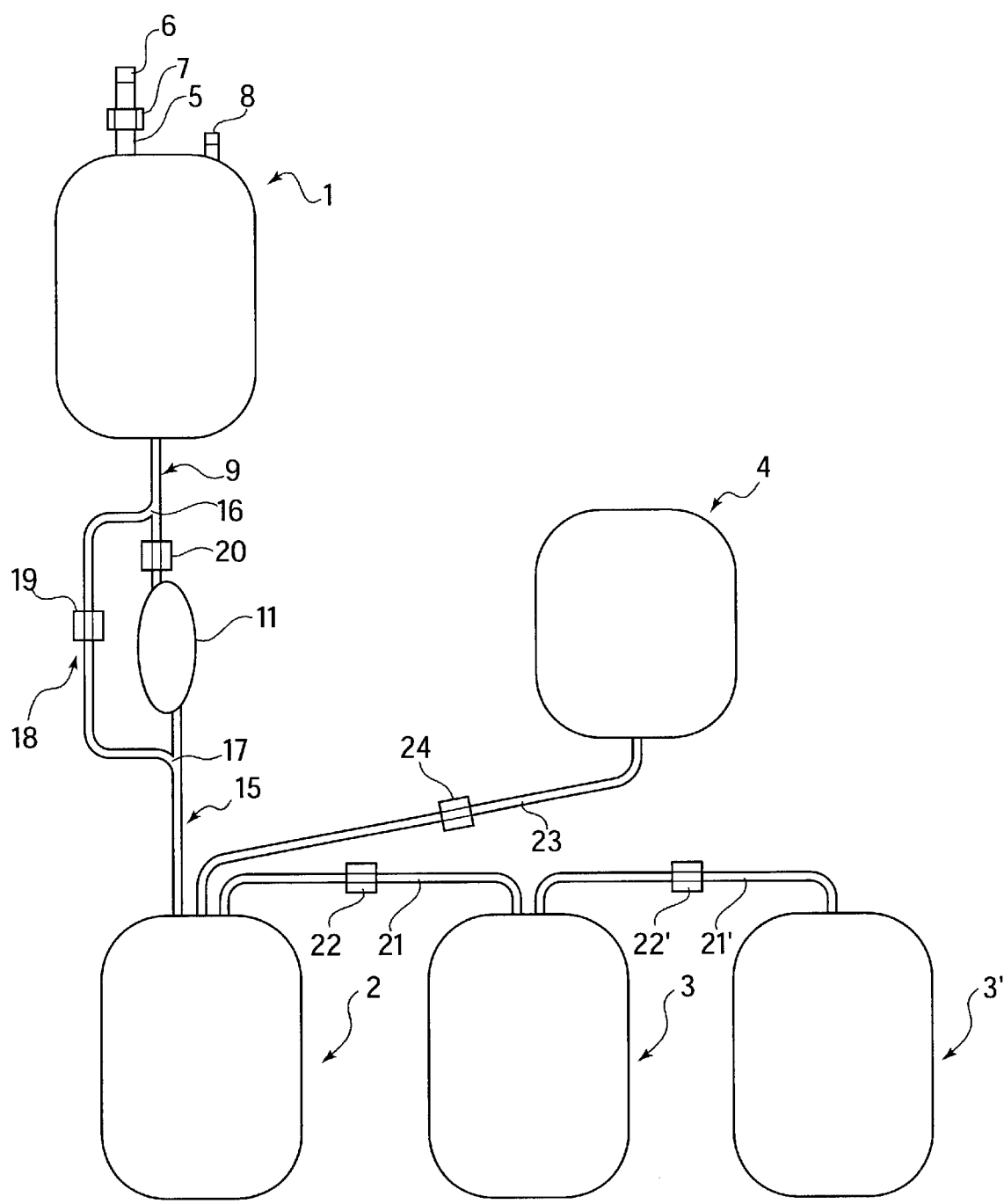
FIG. 3 shows a second specific embodiment of the separating device having two satellite containers.

FIG. 3 shows a second specific embodiment of the separating device. This embodiment is differentiated from the specific embodiments described with reference to FIGS. 1 and 2 with regard to second satellite container 3', which is connected to first satellite container 2 via a second transfer line 21' containing a further hose clamp 22'. In FIG. 3, the parts corresponding to the parts of the separating device in FIGS. 1 and 2 are marked with the same reference numerals. Second satellite container 3', in a further centrifuge step, permits a further separation of the mixed layer of blood plasma and thrombocytes located in first satellite container 3.

What is claimed is:

1. A device for separating blood into blood components comprising a collecting container having a connecting line for receiving blood; a filter for removing leucocytes, which is subdivided by a filter material into two chambers, and which is operable in two directions; a first collecting line connecting the collecting container to the first chamber of the filter; a second collecting line connecting the second chamber of the filter to a primary container; a satellite container connected to the primary container; a bypass line creating a fluid connection between the collecting container and the primary container, wherein the bypass line circumvents the filter and allows a liquid to flow between the collecting container and the primary container; means for opening and closing the bypass line; and means for opening and closing the first collecting line; an additive container connected to the primary container, wherein the additive container contains SAGM solution.

2. The device of claim 1 wherein the first collecting line has a first branchoff and the second collecting line has a second branch-off.

3. A device for separating blood into blood components comprising a collecting container having a connecting line for receiving blood; a filter for removing leucocytes, which is subdivided by a filter material into two chambers, and which is operable in two directions; a first collecting line connecting the collecting container to the first chamber of the filter; a second collecting line connecting the second chamber of the filter to a primary container; a satellite container connected to the primary container; a bypass line creating a fluid connection between the collecting container and the primary container, wherein the bypass line circumvents the filter and allows a liquid to flow between the collecting container and the primary container; means for opening and closing the bypass line; and means for opening and closing the first collecting line;an additive container connected to the primary container, wherein the additive container contains a solution for storing a blood component.

4. The device of claim 3 further comprising at least one secondary satellite container connected to the satellite container by a secondary transfer line, the secondary transfer line having means for opening and closing the line.

5. The device of claim 3 further comprising means for opening and closing the connection between the satellite container and the primary container.

6. The device of claim 3 further comprising means for opening and closing the connection between the additive container and the primary container.

7. The device of claim 3 wherein the first collecting line has a first branch-off and the second collecting line has a second branch-off.

8. A method for separating blood into blood components comprising the steps of:

(a) connecting a source of whole blood to a device for separating blood into blood components, wherein the device comprises a collecting container having a connecting line for receiving blood; a filter for removing leucocytes, which is subdivided by a filter material into two chambers; a first collecting line connecting the collecting container to the first chamber of the filter; a second collecting line connecting the second chamber of the filter to a primary container; a satellite container connected to the primary container; a bypass line creating a fluid connection between the collecting container and the primary container which circumvents the filter; means for opening and closing the bypass line; means for opening and closing the first collecting line; an additive container connected to the primary container; and means for opening and closing the connection between the additive container and the primary container;

(b) collecting whole blood in the collecting container;

(c) conveying the blood collected in the collecting container, via the bypass line, into the primary container;

(d) centrifuging whole blood in the primary container to separate whole blood into an erythrocyte layer and a mixed layer of blood plasma and thrombocytes;

(e) conveying the mixed layer of blood plasma and thrombocytes from the primary container into the satellite container;

(f) conveying an additive agent from the additive container into the primary container; and (g) conveying erythrocytes suspended in the additive agent from the primary container through the second collecting line, the leucocyte filter, and the first collecting line into the collecting container.

9. The method of claim 8, further comprising the steps of sealing or clamping off the collecting container and disconnecting the collecting container from the device.

\* \* \* \* \*